United States Patent [19]

Miller et al.

[11] Patent Number: 5,158,875
[45] Date of Patent: Oct. 27, 1992

[54] PRODUCTION OF BIOLOGICALLY ACTIVE INSULIN-LIKE GROWTH FACTOR I FROM HIGH EXPRESSION HOST CELL SYSTEMS

[75] Inventors: James A. Miller, Agoura; Philip K. Hsieh, Thousand Oaks; Larry B. Tsai, Agoura, all of Calif.

[73] Assignee: Amgen Inc., Thousand Oaks, Calif.

[21] Appl. No.: 398,699

[22] Filed: Aug. 25, 1989

[51] Int. Cl.$^5$ .................. C12P 21/02; C12P 21/06; C07K 7/40; C07K 7/10

[52] U.S. Cl. .................. 435/69.1; 530/303; 530/305; 530/324; 530/399; 435/69.4; 435/69.7

[58] Field of Search .................. 435/68.1, 69.1, 69.4, 435/69.7, 172.3; 530/303, 324, 344, 399; 935/47, 49, 51

[56] References Cited

U.S. PATENT DOCUMENTS 4,532,207 7/1985 Brewer et al. .................. 435/69.4

FOREIGN PATENT DOCUMENTS 8810299 12/1988 World Int. Prop. O. .

OTHER PUBLICATIONS

Peters, M. A. 1985, "Expression of a biologically active analogue of somatomedin-c/insulin-like growth factor I", *Gene,* vol. 35, pp. 83-89.

*Primary Examiner*—Richard A. Schwartz
*Assistant Examiner*—Mary E. Mosher
*Attorney, Agent, or Firm*—Julia E. Abers

[57] ABSTRACT

A novel method for refolding reduced IGF-I is provided in accordance with the present invention. The method is carried out by providing additional positive charge at the amino terminal end of the IGF-I molecule by the presence of a short leader sequence. The additional positive charge on the met-end of the IGF-I molecule has been found to enable recombinant IGF-I to refold simply by stirring solubilized inclusion body protein for between 2–16 hours, or overnight. The present invention also provides a novel fusion protein intermediate of IGF-I attached to the positively charged leader sequence.

7 Claims, 2 Drawing Sheets

PRODUCTION OF BIOLOGICALLY ACTIVE INSULIN-LIKE GROWTH FACTOR I FROM HIGH EXPRESSION HOST CELL SYSTEMS

BACKGROUND

Advances in recombinant DNA technology in recent years have made possible the production of significant quantities of foreign proteins of interest in host cells. Recombinant proteins are produced in host cell systems by transfecting the host cells with DNA coding for the protein of interest, and then growing the transfected host cells under conditions which favor expression of the new recombinant protein by the host cell. Where the recombinant protein of interest is highly expressed by a particular host cell system, these exogenous proteins are typically precipitated within the host cell as inclusion bodies. High levels of expression, and consequent deposition of the recombinant protein in the form of inclusion bodies, is more likely to occur where procaryotic host cells are employed.

The procaryote *E. coli* is commonly selected for use in high expression systems, in part, because *E. coli* host cells tend to be more amenable to the production of extremely large quantities of recombinant protein. Low expression host cell systems, typically those employing eucaryotic host cells and yeast host cells, fail to produce recombinant protein in the tremendous quantities generated in high expression host cell systems. While expressed in relatively low quantities, however, recombinant proteins from these lower expression host cells are more likely to be recovered in their biologically active form, due to the tendency of low expression host cells to secrete the exogenous recombinant protein into the aqueous medium surrounding the host cell, rather than to deposit the protein in the high density inclusion bodies.

The trade-off with higher expression systems is that, in return for obtaining higher yields of recombinant product, the recombinant protein must be isolated from inclusion bodies. This typically requires refolding of the denatured protein in order to generate biologically active product. Both the difficulty and the success of efforts to refold recombinant proteins varies significantly with the particular protein being produced.

One recombinant protein which has become of particular interest in the wake of recent advances in recombinant DNA technology is a growth factor known as insulin-like growth factor I (IGF-I). IGF-I is known to consist of 70 amino acids, as is shown in the following sequence:

IGF is biologically active only in its refolded form. The IGF-I molecule contains six cysteine residues, all of which form disulfide bonds which hold the molecule in its biologically active refolded form.

The difficulty inherent in obtaining biologically active recombinant proteins from high expression host cell systems is particularly difficult in the case of IGF-I due to the tendency of the IGF-I molecule to form stable, but incorrect disulfide bonds, which result in inactive, or only partially active, conformers. Moreover, typical methods of refolding IGF-I may result in a mixture of these conformers, which are then very difficult to separate. Procaryotic hosts thus have not been found to produce active recombinant IGF-I (rIGF-I) in significant yields (e.g., gram quantities) due to the difficulty in refolding IGF-I and the difficult separation problems.

With respect to recombinant proteins in general, however, refolding methods have been used for transforming denatured recombinant proteins into their active form. U.S. Pat. Nos. 4,511,503 and 4,518,256, for example, describe three refolding procedures which are regarded as being universally applicable, with only minor modifications, to the recovery of biologically active recombinant proteins from inclusion bodies. These procedures recognize that the tertiary, or refolded, structure of proteins is stabilized by hydrogen bonding, hydrophobic interactions, and ionic bonding between amino acid moieties of the protein. When present, it is the disulfide bonding between cysteine moieties that "locks" the tertiary structure in place. These methods therefore seek to eliminate random disulfide bonding prior to coaxing the recombinant protein into its biologically active conformation through its other stabilizing forces.

In one approach, the denatured protein of interest is further purified, under reducing conditions which maintain the cysteine moieties of the protein as free sulfhydryl groups, by supplying a reducing agent throughout all of the purification steps. This permits the protein to refold itself under the conditions of purification, in the absence of incorrect disulfide bond formation. The reducing agent is then diluted into an aqueous solution to enable the refolded protein to form the appropriate disulfide bonds in the presence of air or some other oxidizing agent. This enables refolding to be easily incorporated into the overall purification process. This method works best for recombinant proteins which have relatively uncomplicated tertiary structures in their biologically active forms.

```
        1                                  10
Gly—Pro—Glu—Thr—Leu—Cys—Gly—Ala—Glu—Leu—Val—Asp—

20
Ala—Leu—Gln—Phe—Val—Cys—Gly—Asp—Arg—Gly—Phe—Tyr—Phe—

30
Asn—Lys—Pro—Thr—Gly—Tyr—Gly—Ser—Ser—Ser—Arg—Arg—Ala—

40                              50
Pro—Gln—Thr—Gly—Ile—Val—Asp—Glu—Cys—Cys—Phe—Arg—Ser—

60
Cys—Asp—Leu—Arg—Arg—Leu—Glu—Met—Tyr—Cys—Ala—Pro—Leu—

70
Lys—Pro—Ala—Lys—Ser—Ala
```

In another approach, refolding of the recombinant protein is allowed to occur in the presence of both the reduced (R-SH) and oxidized (R-S-S-R) forms of a sulfhydryl compound. This enables free sulfhydryls and disulfides to be constantly formed and reformed throughout the purification process. The reduced and oxidized forms of the sulfhydryl compound are provided in a buffer having sufficient denaturing power that all of the intermediate conformations of the protein remain soluble in the course of the unfolding and refolding. Urea is suggested as a suitable buffer medium because of its apparent ability to act as both: (1) a weak enough denaturing agent to allow the protein to approximate its correct conformation; and, (2) a strong enough denaturant that the refolding intermediates maintain their solubility. This approach also works best where the recombinant inclusion body proteins of interest have relatively uncomplicated folding patterns.

A third approach, which is used in more difficult refolding situations, is designed to first break any disulfide bonds which may have formed incorrectly during isolation of the inclusion bodies, and then to derivatize the available free sulfhydryl groups of the recombinant protein. This is accomplished by sulfonating the protein to form a protein-S-SO$_3$ bond. The resulting protein-S-sulfonate solution is then diluted into an aqueous solution where proper refolding is allowed to occur in the absence of incorrect disulfide bond formation. A system containing a sulfhydryl compound (R-SH) and a small percentage of its corresponding oxidized form (R-S-S-R), is then added to the aqueous solution. The pH is adjusted (raised) to a value such that the sulfhydryl compound (R-SH) is at least partially in ionized form (R-S-) so that nucleophilic displacement of the sulfonate is enhanced. While the sulfhydryl compound is sufficient to effect conversion of the protein-S-sulfonate to the appropriate disulfide binding partner, the presence of an oxidized form is required to insure that suitable disulfide bonds will remain intact.

These refolding methods have not been shown to work efficiently with rIGF-I and/or are burdensome and expensive to perform.

In addition, methods have been suggested for preparing IGF-I as a fusion protein. For example, European Patent Application No. 219,814 discloses a process for preparing IGF-I fused with a "protective peptide". These methods employing fusion proteins, however, generally require a relatively long leader sequence, and are directed to improving expression of the inclusion body protein, not to improving refolding of the denatured recombinant protein.

Accordingly, it is an object of the present invention to provide a method for the isolation and purification of biologically active rIGF-I from high expression host cell systems.

SUMMARY OF THE INVENTION

The present invention provides a novel method for refolding reduced IGF-I. The method of the present invention makes use of a fusion protein intermediate which is also new. The fusion protein incorporates a leader sequence which imparts additional positive charge to the amino terminal, or met-end, of the IGF-I molecule. Surprisingly, this additional positive charge on the met-end of the IGF-I molecule enables refolding of rIGF-I to occur simply by stirring solubilized inclusion body protein for between 2-16 hours, or overnight, with resulting yields of the desired IGF-I conformer of around 30-50%.

DETAILED DESCRIPTION OF THE INVENTION

Figure 1:
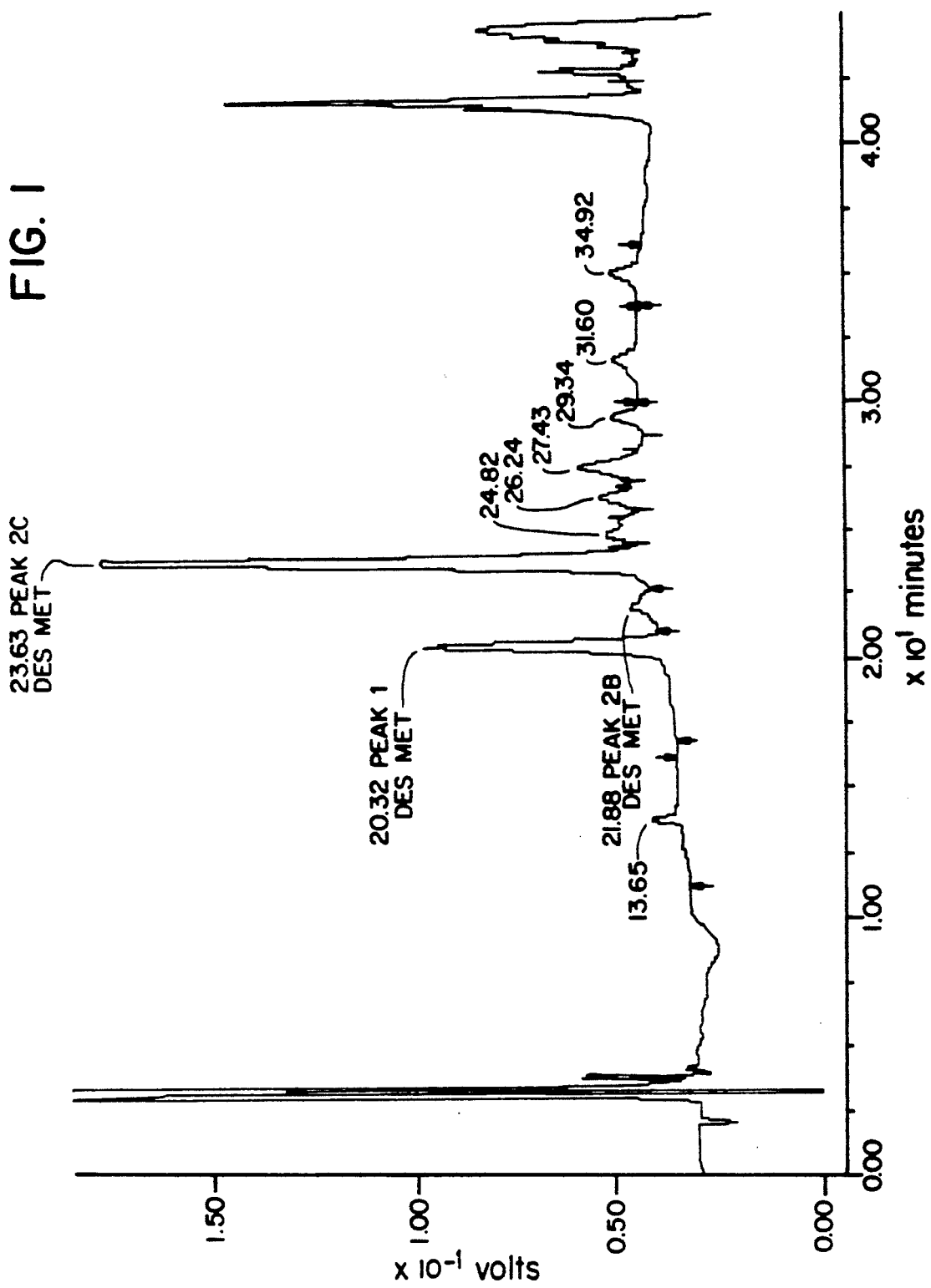
FIG. 1 is a graph of the reversed phase chromatographic separation of IGF-I and various conformers produced in *E. coli* using a lysine leader sequence and a Met-Lys-IGF-I fusion protein intermediate in accordance with the present invention.

The present invention provides a novel method for the recovery of significant amounts of biologically active rIGF-I from *E. coli* or other high expression host cell systems. The method of the present invention is accomplished through the use of a novel fusion protein intermediate which incorporates a positively charged leader sequence on the amino terminal end of the rIGF-I. The positively charged leader sequence imparts additional positive charge to the amino terminus, or met-end, of the rIGF-I molecule, which, like all amino terminal ends of proteins, is already positively charged at or below biological pH. It has surprisingly been found that the positively charged leader sequence at the amino terminal end increases refolding efficiencies and minimizes the tendency of the solubilized inclusion body rIGF-I to refold into spurious conformers and/or aggregates. This method is equally effective for IGF-I analogs requiring the same cysteine bond pattern for the desired biologically active conformer, the desired biologically active conformer being the refolded rIGF-I conformer which, in an in vitro receptor binding assay, exhibits activity substantially similar to naturally occurring IGF. Preferably, the leader sequence is removed prior to purification.

The method of the present invention is carried out in the following steps:

(1) The gene for IGF-I, or an analog thereof, containing the leader sequence of the present invention is cloned and subsequently expressed in a high expression host cell;

(2) The expressed fusion protein is harvested and recovered using standard techniques known to those skilled in the art;

(3) The rIGF-I fusion protein is refolded into its active form;

(4) The rIGF-I fusion protein may also be purified, preferably to homogeneity.

More preferably, the method of the present invention is carried out as follows:

(1) The gene for IGF-I, or an analog thereof, containing the leader sequence of the present invention is cloned and subsequently expressed in a high expression host cell;

(2) The expressed fusion protein is harvested and recovered using standard techniques known to those skilled in the art;

(3) The rIGF-I fusion protein is refolded into its active form;

(4) The leader sequence of the present invention is removed from the rIGF-I fusion protein; and, (5) The resulting rIGF-I may be purified, preferably to homogeneity.

The novel leader sequence used in the method of the present invention is at least one amino acid residue in length. It is preferred that the leader sequence be between 1 and 10 amino acid residues in length, more preferably between 1 and 3 amino acid residues in length. A one amino acid leader sequence is preferred, although leader sequences as long as three amino acids residues have been shown to be at least equally effective as the preferred one amino acid length in enhancing the refolding process. The one amino acid length is preferred for simplicity and ease of handling.

The leader sequence of the present invention begins (i.e., at the amino terminus of the leader sequence) with a positively charged amino acid residue. Preferably the positively charged amino acid residue is selected from the group consisting of lysine, arginine, and histidine. More preferably, the positively charged amino acid is acid is lysine. The leader sequence may then be extended, from either the carboxy or amino end of the leader sequence, with other amino acids residues. Preferably, these other amino acids residues are also positively charged. Most preferably the other amino acids residues are lysine residues. The exact sequence of amino acid residues added to the leader sequence will depend, in part, on the method which is optionally selected for removing the leader sequence following refolding, and will be apparent to one of ordinary skill in the art in light of the teachings discussed below.

It is preferred that the leader sequence be removed after the fusion protein containing the leader sequence has been refolded. Preferably, the leader sequence is removed by the use of an enzyme. Where an enzyme is used to remove the leader sequence, it is preferred that amino acids with side chains which will inhibit cleavage by the enzyme be avoided in adding to the leader sequence. More preferably, the enzyme is a diaminopeptidase. Where a diaminopeptidase is used to remove the leader sequence, it is preferred that an odd number of amino acids be used in the leader sequence. It is further preferred, in certain such an instance, that the use of proline be avoided in lengthening the leader sequence.

More specifically, the method of the present invention is performed by first cloning the IGF-I or IGF-I analog gene with a leader sequence of the present invention as described above. Cloning can be performed according to any one of a number of known methods. Optimal methods using particular host cell systems will be apparent to those skilled in the art. As earlier mentioned, where a diaminopeptidase is being used to remove the leader sequence, it is preferred to use an odd number of amino acids in the leader sequence, so that the methionine residue which is added by procaryotic host cells at the amino end of the foreign IGF-I molecule will be removed at the same time as the leader sequence. A diaminopeptidase, such as Cathepsin C, is particularly preferred as the means for removing the leader sequence, because the enzyme will not cut after a proline residue. Thus, following cutting after the last two amino acid residues of the leader sequence, e.g., the lysine and methionine residues of the Met-Lys-rIGF-I, where a lysine residue is used as the leader sequence, the Cathepsin C will automatically stop cutting. This feature renders Cathepsin C an easily controlled means for removal of the leader sequence.

Following cloning, the inclusion body containing the Met-Leader-IGF-I is solubilized and recovered, again using techniques known in the art. The positively charged leader sequence of the present invention enables refolding to occur under less than rigorous conditions, essentially by stirring under controlled pH, salt, and urea conditions, with the formation of spurious conformers and IGF-I aggregates being significantly minimized. During refolding, it is preferred that the pH be maintained at about 8 to about 11, and that the salt concentration be from about 0 to about 1M.

It is preferred that the leader sequence be removed from the Met-Leader-IGF-I molecule prior to purification. Preferably, the leader sequence is removed enzymatically. Selection of the enzyme and conditions for removal will be determined, in part, by the choice of positively charged leader sequence, and will be apparent to those skilled in the art. Known purification methods can be used.

The following examples are provided to aid in the understanding of the present invention, the true scope of which is set forth in the appended claims. It is understood that modifications can be made in the procedures set forth, without departing from the spirit of the invention.

EXAMPLE 1

Cloning of IGF-I Gene with Lysine Leader Sequence

The following synthetic IGF-I gene, designed for direct expression in high yield in an *E. coli* host was cloned into mp20 bacteriophage and the correct DNA sequence confirmed using known technology. The IGF gene DNA was then cloned into a pCFM1156 expression vector as a XbaI to BamHI DNA restriction fragment.

```
XbaI
                                             MetGlyProGluThrLeuCysGlyAlaGlu
TTCTAGAAGGAGGAATAACATATGGGACCAGAAACATTATGTGGTGCAGAA—
        10                  30                  50

LeuValAspAlaLeuGlnPheValCysGlyAspArgGlyPheTyrPheAsn
CTGGTAGATGCTCTTCAATTCGTATGTGGTGACCGTGGATTTTACTTCAAC—
                  70                  90

LysProThrGlyTyrGlySerSerSerArgArgAlaProGlnThrGly
AAACCGACTGGTTATGGTTCTTCTTCTCGTCGTGCTCCGCAGACTGGT—
        110                 130                 150

IleValAspGluCysCysPheArgSerCysAspLeuArgArgLeuGluMet
ATTCTAGACGAATGTTGCTTTCGTTCTTGCGATCTGCGTCGTTTAGAAATG—
                  170                 190

TyrCysAlaProLeuLysProAlaLysSerAlaEndEnd
```

```
TATTGTGCACCACTGAAACCGGCTAAGTCTGCTTAATAG
    210                 230
```

The plasmid pCFM1156PL can be derived from the described plasmid pCFM836. (See U.S. Pat. No. 4,710,473 hereby incorporated by reference) by destroying the two endogenous NdeI restriction sites, by end filling with T4 polymerase enzyme, followed by blunt end ligation, by replacing the DNA sequence between the unique promoter with a similar fragment obtained from pCFM636 (see U.S. Pat. No. 4,710,473) containing the PL promoter, and by substituting the small DNA sequence between the unique ClaI and KpnI restriction sites with the following oligonucleotide:

```
     ClaI                                                  KpnI
5' CGATTTGATTCTAGAAGGAGGAATAACATATGGTTAACGCGTTGGAATTCGGTAC3'
3'     TAAACTAAGATCTTCCTCCTTATTGTATACCAATTGCGCCAACCTTAAGC    5'
```

The PL promoter DNA sequence is inserted as follows:

```
      AatII
5'       CTAATTCCGCTCTCACCTACCAAACAATGCCCCCCTGCAAAAAATAAA—
3' TGCAGATTAAGGCGAGAGTGGATGGTTTGTTACGGGGGGACGTTTTTTATTT—

—TTCATATAAAAAACATACAGATAACCATCTGCGGTGATAAATTATCTCTGGCGG—
—AAGTATATTTTTTGTATGTCTATTGGTAGACGCCACTATTTAATAGAGACCGCC—

—TGTTGACATAAATACCACTGGCGGTGATACTGAGCACAT   3'
—ACAACTGTATTTATGGTGACCGCCACTATGACTCGTGTAGC 5'
                                         ClaI
```

To construct the Lys-IGF-I gene for use in conjunction with diaminopeptidase enzyme, a synthetic DNA oligonucleotide was synthesized with the following sequence:

```
   NdeI
5' TATGAAAGGACCAGAAACATTATGTGGTGCAGAACTGGTAGATGCTCTTC
3'     ACTTTCCTGGTCTTTGTAATACACCACGTCTTGACCATCTACGAGAAG

—AATTCGTAGTG      3'
—TTAAGCATACACCACTG 5'
          BstEII
```

This sequence was then inserted into the pCFM1156-Met1-IGF-I plasmid by replacing the DNA at the amino terminal end of the IGF-I gene between the unique restriction sites NdeI and BstEII. The new construct, pCFM1156-Lys-IGF-I now produces a protein with a met-lys-gly-pro- . . . amino terminus. This sequence is an ideal substrate for the diaminopeptidase enzyme, with the resulting proteolytic cleavage giving the same gly-pro amino terminus as is found in naturally occurring mammalian IGF-I.

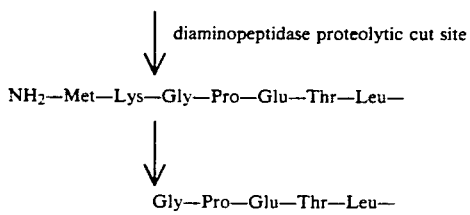

EXAMPLE 2

Recovery and Solubilization of Inclusion Bodies

Inclusion bodies containing the Met-Lys-rIGF-I were isolated from *E. coli*. The harvested paste was broken by a Gaulin homogenizer and the inclusion bodies were recovered by centrifugation. The inclusion bodies were then washed once with 1% deoxycholate and once with water.

Washed inclusion bodies were then solubilized by stirring with 10 volumes of 8 M urea at pH 3.5 for one hour. This low pH solubilization prevented spontaneous oxidation of the sulfhydryl groups during solubilization and is vital to obtaining optimal recovery.

EXAMPLE 3

Refolding of Solubilized Met-Lys-IGF-I Fusion Protein

Following solubilization as set forth in Example 2, the 8M urea solution was diluted ten-fold to a final concentration of 0.1–0.5 mg/mL Met-Lys-rIGF-I fusion protein in 0.8M urea and adjusted to 0.5M NaCl. The pH of the solution was adjusted to 10.5 and stirred two hours at room temperature. This mixture of pH and salt concentration is vital for optimal refolding, as at pH 9.5, without salt the efficiency for folding into the proper conformation dropped 50-fold.

After two hours of stirring, the refolding and oxidation was terminated by adjusting the pH of the solution to 5.2. The solution was then clarified by centrifugation or filtration. An aliquot of the clarified solution was analyzed by reversed phase chromatography, as shown in FIG. 1. It can be seen from FIG. 1 that the desired rIGF-I refolded product, Peak 2C, is present in considerable excess of the most significant conformers, represented by Peaks 1 and 2B. The relative amounts of the desired product and contaminating conformers are shown in Table I, below:

TABLE I

| Peak No. | Component Name | Retention Time (min.) | Peak Area | Area Percent |
|---|---|---|---|---|
| 2 | Peak 1 | 20.317 | 1527100 | 20.20 |
| 3 | Peak 2B | 21.875 | 282269 | 3.73 |
| 4 | Peak 2C | 23.625 | 3681520 | 48.69 |

The clarified solution was then concentrated and diafiltered with 10 mM sodium acetate, pH 5.4, on a 3000 $M_W$ cutoff membrane.

EXAMPLE 4

Removal of the Met-Lys Leader Sequence with Cathepsin C

The concentration of the clarified and concentrated Met-Lys-rIGF-I fusion protein solution from Example 3 was adjusted to between 0.5 and 2 mg/mL with 20 mM sodium acetate pH 5.4 buffer. A solution of the diaminopeptidase beef spleen cathepsin C (EC#3.4.14.1), containing approximately 10 U/mL activity, was made in 10 mM cysteamine and allowed to incubate for 15 minutes at room temperature. This enzyme solution was then added to the crude Met-Lys-rIGF-I fusion protein solution to obtain a final activity concentration of 0.025 U/mL. This reaction was allowed to proceed overnight (12-16 hours) at room temperature. The extent of the reaction was monitored by high performance ion exchange chromatography, which resolved Met-Lys-rIGF-I from the rIGF-I cleavage product on the basis of the extra positive charge present on Met-Lys-rIGF-I fusion protein. Greater than 90% of the Met-Lys-rIGF-I fusion protein was enzymatically cleaved to the natural sequence IGF-I.

EXAMPLE 5

Purification to Remove E. coli Proteins, Spurious Conformers of IGF-I, and Residual Met-Lys-IGF-I The cleavage mixture was clarified by filtration through a 0.45μ membrane, after which it was pumped onto a standard chromatography column packed with C4-derivatized silica. Ideally, the column contained 500 g of C4-silica per kilogram of E. coli cell paste used in the purification. The loaded column was then washed with two column volumes of 26% ethanol, 12.5 mM HCl, and eluted with a 10 column volume gradient of 26-31% ethanol, 12.5 mM HCl.

To remove residual Met-Lys-rIGF-I fusion proteins, ion exchange chromatography was performed. Fractions from the reverse phase column containing the desired biologically active conformer of rIGF-I were applied to an S-Sepharose ® (Pharmacia, Uppsala, Sweden) column, the column being loaded with the product of 1 kg of cell paste per 300 mL of resin. The loaded column was then washed with 8 column volumes of 20 mM sodium acetate, pH 5.4, containing 50 mM NaCl. The rIGF-I was then eluted with 50-200 mM NaCl gradient in the 20 mM sodium acetate, pH 5.4 buffer. Being more positively charged, the Met-Lys-rIGF-I fusion protein binds to the resin more tightly than natural sequence rIGF-I and was thus removed from the desired rIGF-I product.

EXAMPLE 6

E. coli-Produced Met-IGF-I from Conventional Methods

Figure 2:
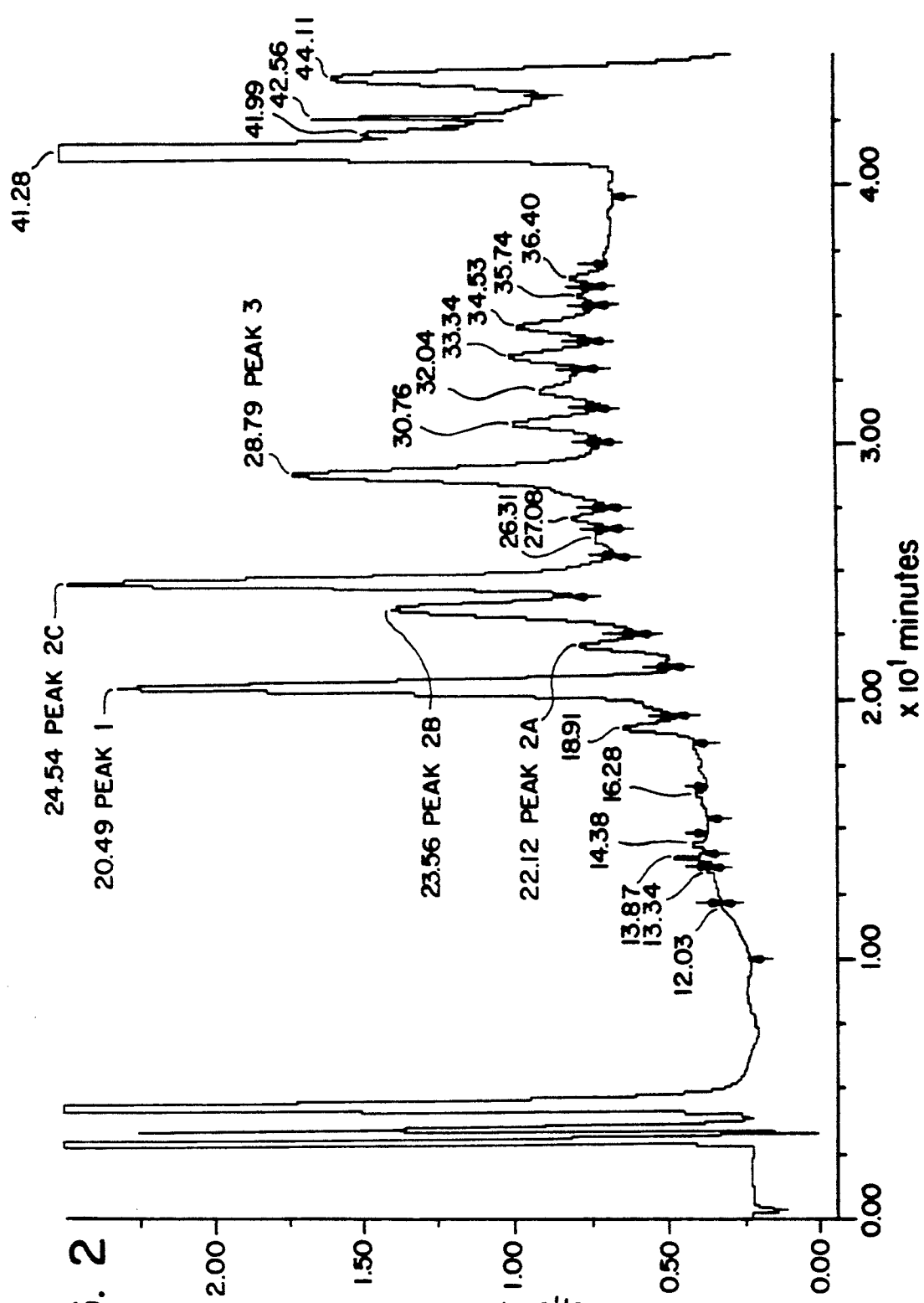
FIG. 2 is a graph of the reversed phase chromatographic separation of met-IGF-I and various conformers produced in *E. coli* using an IGF-I coding sequence without benefit of a charged leader sequence.

Met-rIGF-I was produced in an E. coli host cell according to Examples 1, 2, 3, and 5 with the exception that no leader sequence was added to the met1-IGF. This resulted in extremely poor refolding efficiencies, and no further purification was therefore pursued. The same Met-rIGF-I, produced without a positively charged leader sequence, was then refolded using a sulfonation technique similar to that described in U.S. Pat. Nos. 4,511,503 and 4,518,256, described in the background. The results of the chromatographic separation are shown in FIG. 2. It can be seen from FIG. 2 that the most significant conformers, represented by Peaks 1, 2B, and 3, are present to a much greater extent than in the refolded conformer solution which results where the leader sequence of the present invention is used. The desired rIGF-I refolded product, Peak 2C, is present in much lower quantity. The relative amounts of the desired product and contaminating conformers are shown in Table II, below:

TABLE II

| Peak No. | Component Name | Retention Time (min.) | Peak Area | Area Percent |
|---|---|---|---|---|
| 7 | Peak 1 | 20.494 | 6083306 | 14.94 |
| 9 | Peak 2B | 23.559 | 4198836 | 10.31 |
| 10 | Peak 2C | 24.539 | 6999989 | 17.19 |
| 13 | Peak 3 | 28.793 | 6224412 | 15.28 |

What is claimed is:

1. A method for producing insulin-like growth factor I (IGF-I) from a high expression host cell comprising:
   (a) expressing a gene encoding Met-Lys-IGF-I in a high expression host cell;
   (b) harvesting said Met-Lys-IGF-I from said high expression host cell; and
   (c) refolding said Met-Lys-IGF-I into its biologically active conformation.

2. The method of claim 1 wherein said refolded Met-Lys-IGF-I is purified.

3. The method of claim 1 wherein the Met-Lys leader sequence of said Met-Lys-IGF-I is removed following refolding to produce a refolded IGF-I.

4. The method of claim 3 wherein said refolded IGF-I is purified.

5. The method of claim 3 wherein said Met-Lys leader sequence is removed by the action of a diaminopeptidase.

6. The method of claim 5 wherein said diaminopeptidase is Cathepsin C.

7. A fusion protein consisting of Met-Lys-IGF-I.